United States Patent
Bowers

(10) Patent No.: US 10,657,796 B2
(45) Date of Patent: *May 19, 2020

(54) METHOD AND SYSTEM FOR EXPEDITING THE RESCUE OF VICTIMS EXPERIENCING SUDDEN CARDIAC ARREST (SCA) WHEN USED IN CONJUNCTION WITH AN AUTOMATED EXTERNAL DEFIBRILLATOR (AED)

(71) Applicant: Scion Medical Limited, Mong Kok (HK)

(72) Inventor: Kyle R. Bowers, Boxborough, MA (US)

(73) Assignee: Scion Limited Medical, Mong Kok (HK)

(*) Notice: Subject to any disclaimer, the term of this patent is extended or adjusted under 35 U.S.C. 154(b) by 0 days.

This patent is subject to a terminal disclaimer.

(21) Appl. No.: 15/358,830

(22) Filed: Nov. 22, 2016

(65) Prior Publication Data

US 2017/0294107 A1    Oct. 12, 2017

Related U.S. Application Data

(63) Continuation of application No. 12/911,393, filed on Oct. 25, 2010.

(60) Provisional application No. 61/279,634, filed on Oct. 23, 2009.

(51) Int. Cl.
| | | |
|---|---|---|
| G08B 25/01 | (2006.01) | |
| A61B 5/0205 | (2006.01) | |
| A61B 5/0408 | (2006.01) | |
| A61N 1/39 | (2006.01) | |
| G08B 25/08 | (2006.01) | |

(Continued)

(52) U.S. Cl.
CPC ........ *G08B 25/016* (2013.01); *A61B 5/02055* (2013.01); *A61B 5/0408* (2013.01); *A61B 5/1112* (2013.01); *A61B 5/6833* (2013.01); *A61N 1/39* (2013.01); *G08B 25/08* (2013.01); *G08B 25/12* (2013.01); *G09B 23/288* (2013.01); *A61B 5/021* (2013.01); *A61B 5/024* (2013.01); *A61B 5/053* (2013.01); *A61B 5/14542* (2013.01); *A61B 2505/01* (2013.01); *A61B 2560/0431* (2013.01)

(58) Field of Classification Search
CPC .................................................. A61B 5/02055
See application file for complete search history.

(56) References Cited

U.S. PATENT DOCUMENTS 5,228,449 A * 7/1993 Christ ................ A61B 5/02433
379/38
5,593,426 A * 1/1997 Morgan .................... A61N 1/39
128/903

(Continued)

*Primary Examiner* — Carl H Layno
*Assistant Examiner* — Jennifer L Ghand
(74) *Attorney, Agent, or Firm* — Pandiscio & Pandiscio

(57) ABSTRACT

A method and system for expediting the rescue of victims experiencing sudden cardiac arrest (SCA) when used in conjunction with an automated external defibrillator (AED). The system involves an apparatus that calls for help (i.e. 911), detects SCA and cardiac arrhythmias, locates an AED, guides the rescuer through CPR and connection of the AED. A second apparatus is in the enclosure that contains the AED, sends location information to the other apparatus, triggers audible and visual indicators, and provides information on the victim's location.

20 Claims, 10 Drawing Sheets

(51) Int. Cl.
  *G08B 25/12*    (2006.01)
  *G09B 23/28*    (2006.01)
  *A61B 5/00*     (2006.01)
  *A61B 5/11*     (2006.01)
  *A61B 5/053*        (2006.01)
  *A61B 5/021*        (2006.01)
  *A61B 5/024*        (2006.01)
  *A61B 5/145*        (2006.01)

(56) References Cited

U.S. PATENT DOCUMENTS

| | | |
|---|---|---|
| 6,292,687 B1 | 9/2001 | Lowell et al. |
| 6,658,290 B1 | 12/2003 | Lin et al. |
| 8,577,475 B2 | 11/2013 | Bowers |
| 9,498,152 B2 | 11/2016 | Bowers |
| 2002/0087194 A1 | 7/2002 | Russell |
| 2003/0025602 A1 | 2/2003 | Medema et al. |
| 2003/0212311 A1 | 11/2003 | Nova et al. |
| 2003/0233129 A1 | 12/2003 | Matos |
| 2004/0027245 A1 | 2/2004 | Schlager et al. |
| 2006/0055536 A1 | 3/2006 | Jackson |
| 2006/0155336 A1 | 7/2006 | Heath |
| 2006/0270952 A1 | 11/2006 | Freeman et al. |
| 2007/0219588 A1 | 9/2007 | Freeman |
| 2007/0270909 A1 | 11/2007 | Saketkhou |
| 2007/0276300 A1 | 11/2007 | Olson et al. |
| 2008/0177341 A1 | 7/2008 | Bowers |
| 2010/0234700 A1* | 9/2010 | Bowers ................ A61B 5/0006 600/301 |
| 2011/0152702 A1 | 6/2011 | Goto |

* cited by examiner

Example Wireless Method

METHOD AND SYSTEM FOR EXPEDITING THE RESCUE OF VICTIMS EXPERIENCING SUDDEN CARDIAC ARREST (SCA) WHEN USED IN CONJUNCTION WITH AN AUTOMATED EXTERNAL DEFIBRILLATOR (AED)

REFERENCE TO PENDING PRIOR PATENT APPLICATION

This patent application is a continuation of prior U.S. patent application Ser. No. 12/911,393, now U.S. Pat. No. 9,498,152, filed Oct. 25, 2010 by Kyle R. Bowers for METHOD AND SYSTEM FOR EXPEDITING THE RESCUE OF VICTIMS EXPERIENCING SUDDEN CARDIAC ARREST (SCA) WHEN USED IN CONJUNCTION WITH AN AUTOMATED EXTERNAL DEFIBRILLATOR (AED), which claims benefit of prior U.S. Provisional Patent Application Ser. No. 61/279,634, filed Oct. 23, 2009 by Kyle R. Bowers for METHOD AND SYSTEM FOR EXPEDITING THE RESCUE OF VICTIMS EXPERIENCING SUDDEN CARDIAC ARREST (SCA) WHEN USED IN CONJUNCTION WITH AN AUTOMATED EXTERNAL DEFIBRILLATOR (AED)

FIELD OF THE INVENTION

This invention relates to a method and system for expediting the rescue of victims experiencing sudden cardiac arrest (SCA) when used in conjunction with an automated external defibrillator (AED). The system involves an apparatus that calls for help (i.e., 911), detects SCA and cardiac arrhythmias, locates an AED, guides the rescuer through CPR and connection of the AED. A second apparatus is in the enclosure that contains the AED, sends location information to the other apparatus, triggers audible and visual indicators, and provides information on the victim's location.

BACKGROUND OF THE INVENTION

Approximately 350,000 deaths occur each year in the United States alone due to Sudden Cardiac Arrest (SCA). Worldwide deaths due to Sudden Cardiac Arrest (SCA) are believed to be at least twice that of the United States. Many of these deaths can be prevented if effective defibrillation is administered within 3-5 minutes of the onset of SCA.

Sudden Cardiac Arrest (SCA) is the onset of an abnormal heart rhythm, lack of pulse and absence of breath, leading to a loss of consciousness. If a pulse is not restored within a few minutes, death occurs. Most often, SCA is due to Ventricular Fibrillation (VF), which is a chaotic heart rhythm that causes an uncoordinated quivering of the heart muscle. The lack of coordinated heart muscle contractions results in a lack of blood flow to the brain and other organs. Unless this chaotic heart rhythm is quickly terminated, thereby allowing the heart to restore its own normal rhythm, death ensues.

Rapid detection, CPR and defibrillation are the only known means to restore a normal heart rhythm and prevent death after SCA due to Ventricular Fibrillation (VF). For each minute that passes after the onset of SCA, mortality typically increases by 10%. At 7-10 minutes, the survival rate is generally below 10%. However, if a patient is effectively defibrillated within 1-2 minutes of the onset of SCA, survival rates can be as high as 90% or more. Therefore, the only known way to increase the chance of survival for an SCA victim through early detection, CPR and defibrillation.

Rescuers require AED training (also CPR and first aid) by the Red Cross, AHA or other organization on what do during the time when someone has a heart attack until help arrives. The steps that rescuers are trained to perform are:
1. Call for help. Dial 911 (in the USA) or have someone else do it for you.
2. Assess the victim's condition:
   a) Move the victim's arm and ask or yell "are you okay?"
   b) Check to see if the person is breathing
3. Call for an AED. Most public places have an AED. Ask someone to locate the nearest AED available.
4. Begin CPR. The American Heart Association has recently changed guidelines to encourage lay rescuers (or even bystanders) to perform CPR compressions.
5. Use an AED if available.

Until recently, first-aid classes taught would-be rescuers to check for a pulse at step (2b) before starting CPR. The AHA now discourages checking for a pulse in an unconscious victim. This is largely because the AHA has found that poorly trained rescuers come to an incorrect conclusion when checking for a pulse in about 35% of cases.

AEDs can easily be found in most public and private places such as schools, golf courses, casinos, restaurants, amusement parks, etc. and have been mandated on airplanes in the USA. As the number of AEDs placed in use increases, so does access to these devices.

SUMMARY OF THE INVENTION

As the number of AEDs placed in use increases, so does the number of lay rescuers and potentially untrained bystanders that will use these devices. In an emergency situation, the lay rescuer may fail to correctly perform the steps as described above or potentially leave a step out. In addition, the lay rescuer may be hesitant to place defibrillation electrodes on a victim's chest, because they are unsure of their condition. This supports the AHAs decision for the lay rescuer to not check for a pulse. As described in the background of the invention, the victim's chances for survival decreases with the time of detection and defibrillation. Therefore the lay rescuer or other bystander must quickly locate the AED, while CPR is being administered.

The inventor sees the need for a system that expedites the rescue of a victim experiencing SCA. The system of the present invention increases the chances of survival of an SCA victim by decreasing the amount of time to complete steps 1-5. In addition, the system described in the present invention performs the sequential steps, where possible, without error or omission.

The system involves first an apparatus that:
(1) calls for help
(2) detects SCA
(3) guides a bystander to the location of a nearby AED
(4) guides the rescuer through CPR and provides information to the rescuer with regard to the efficacy of the CPR being administered
(5) guides the rescuer on how to connect an AED.

In addition, the system involves a second apparatus located with an AED that:
(1) provides the first apparatus with information with regard to the location of the AED
(2) alerts with audible and visual indicators (3) provides information with regard to the location of the victim.

In addition, the system involves a method for expediting the rescue of a victim experiencing SCA. The inventor believes this method, that those skilled in the art will appreciate, will completely change the thinking of how AEDs are used and deployed. Previous thinking included a "Universal Access To Defibrillation" method. This method included widespread deployment of AEDs everywhere. Such an example is walking into an office or other public building, looking for a fire extinguisher and finding an AED located above or in the same enclosure. Disadvantages to this method are, of course, primarily related to the cost of increasing the number of AEDs within a location and the associated costs with servicing, maintenance, etc. of these devices. The inventor believes this new method and system for expediting the rescue of victims experiencing SCA has a large advantage over this previous method. The inventor will introduce an example scenario before the advantages are discussed.

An example scenario of the new paradigm is: victim is discovered potentially experiencing SCA, the rescuer locates a first device, located with a fire extinguisher or other known place, applies the device to the patient, the device calls 911 for EMS dispatch, with location of the victim and also calls on-site trained rescue personnel if available. The device then analyzes the patient for SCA and guides potentially a second rescuer to the location of the nearest AED. The first rescuer is then guided through administering CPR. The second rescuer locates the AED which is being indicated by the AED enclosure. The secondary rescuer or on-site trained rescuer (previously notified by the system) removes the AED and then receives verbal instructions on location of the victim. The first rescuer has now administered CPR for approximately 1-2 minutes. If the device instructs the rescuer to attach the AED, the AED is connected and a defibrillation shock is delivered. In an ideal world, the victim has been converted to a normal sinus rhythm. EMS (previously notified by the system) arrives shortly, stabilizes the victim and transports them to the local hospital or clinic.

Advantages of the new method and system are obvious: the wide-spread deployment of the first device (as described above), which costs a fraction of the cost of an AED and is easier to service, maintain, etc. used in concert with nearby AED with a secondary device (for location) decreases overall cost of the system and expedites the time a victim experiencing SCA is rescued, ultimately giving the victim the optimal chances for survival. There are also other advantages that those skilled in the art will not find obvious and are described in detail below.

BRIEF DESCRIPTION OF THE DRAWINGS

These and other objects and features of the present invention will be more fully disclosed or rendered obvious by the following detailed description of the preferred embodiments of the present invention, which are to be considered together with the accompanying drawings wherein like numbers refer to like elements and further wherein.

DETAILED DESCRIPTION OF THE PREFERRED EMBODIMENTS

Figure 1:
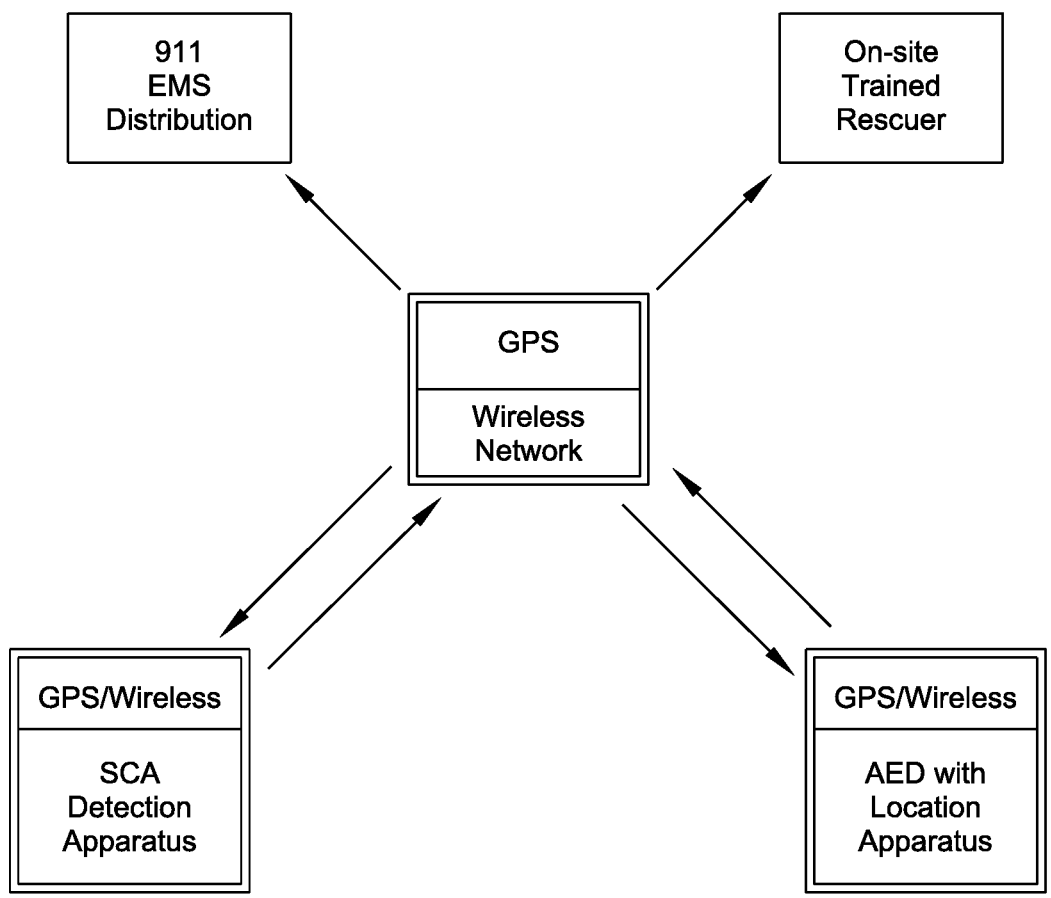
FIG. 1 is block diagram of the system for expediting the rescue of victims experiencing SCA.

A block diagram of the system for expediting the rescue of victims experiencing SCA is shown in FIG. 1. The first device as described in the above summary is referred to as the SCA detection apparatus, since its primary function is to quickly assess the victim and detect or determine if the patient is experiencing SCA. The second device as described in the above summary is referred as the location apparatus, since its primary function is to locate the AED and then locate the victim once the AED has been removed from its enclosure.

Figure 2:
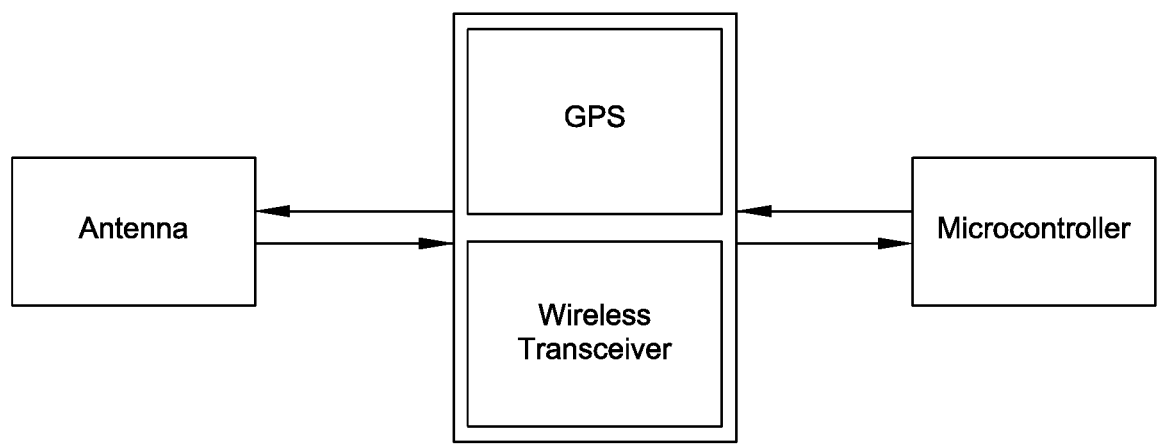
FIG. 2 is a block diagram of the wireless system contained in the SCA detection.

In accordance with one preferred form of the present invention, the SCA detection and location apparatuses contain a wireless system and global positioning system (GPS) as shown in FIG. 2. As those skilled in the art can appreciate, the wireless system may be of any of the current or future wireless networks or technologies. Some examples of current technologies are Bluetooth, Wi-Fi, Zigbee, etc. In accordance with one preferred form of the present invention, the apparatuses contain cell phone electronics and use cellular networks. In accordance with one preferred form of the present invention, the SCA detection is able to "call" the wireless network, contacting dispatch for emergency medical services (EMS) dispatch and provides GPS location of the victim. The SCA apparatus, if pre-programmed, is also able to "call" an on-site trained rescuer. An on-site trained rescuer could range from, for example, a security guard trained in CPR to an emergency physician.

Figure 9:
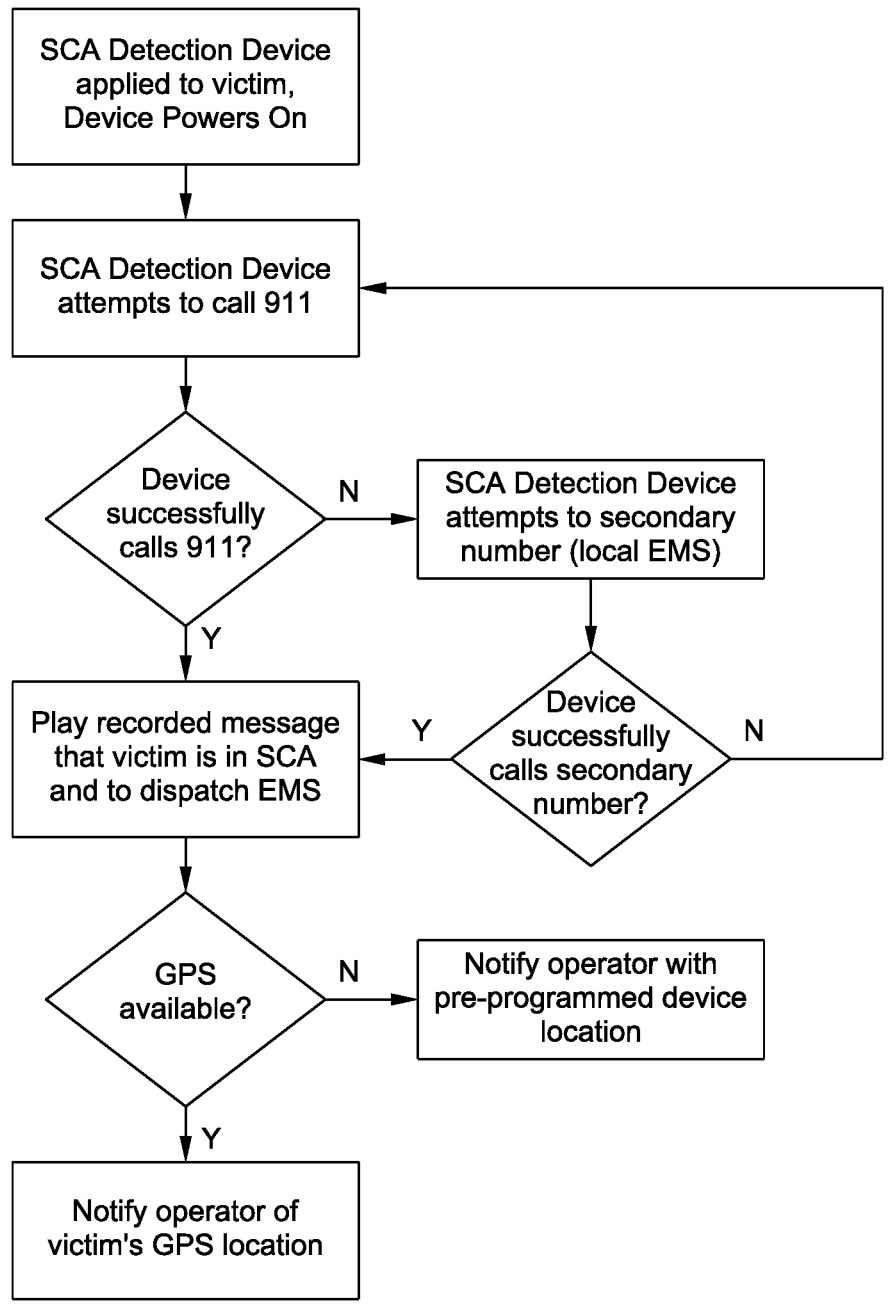
FIG. 9 is a flow diagram showing an example of the wireless method used by the SCA detection.

As shown in the example method in FIG. 9, the SCA detection apparatus continues to attempt to call a secondary number in the event that a primary number is busy, out-of-service, etc. In this example, the primary number is 911 and the secondary number is local EMS, however, the numbers called by the apparatus may not be limited to emergency services.

In accordance with one preferred form of the present invention, the SCA detection apparatus may have a list of prioritized numbers that are called. The prioritized list may change dynamically as the numbers are called and connections are made or not made. As those skilled in the art can appreciate, the example method shown in FIG. 9 is done as a background task, so as not to affect the rapid detection of SCA and to make every attempt possible to ensure help is on the way.

The SCA apparatus device has a voice synthesizer and can transmit messages during the call. In addition, the SCA device is able to locate using GPS and "call" a nearby AED via the location apparatus, notify the location apparatus that an event has occurred and gives the GPS location of the victim. As those skilled in the art can appreciate, there are no limitations to this network and more wireless branches of any kind could be added to the system diagram shown in FIG. 1.

Figure 3:
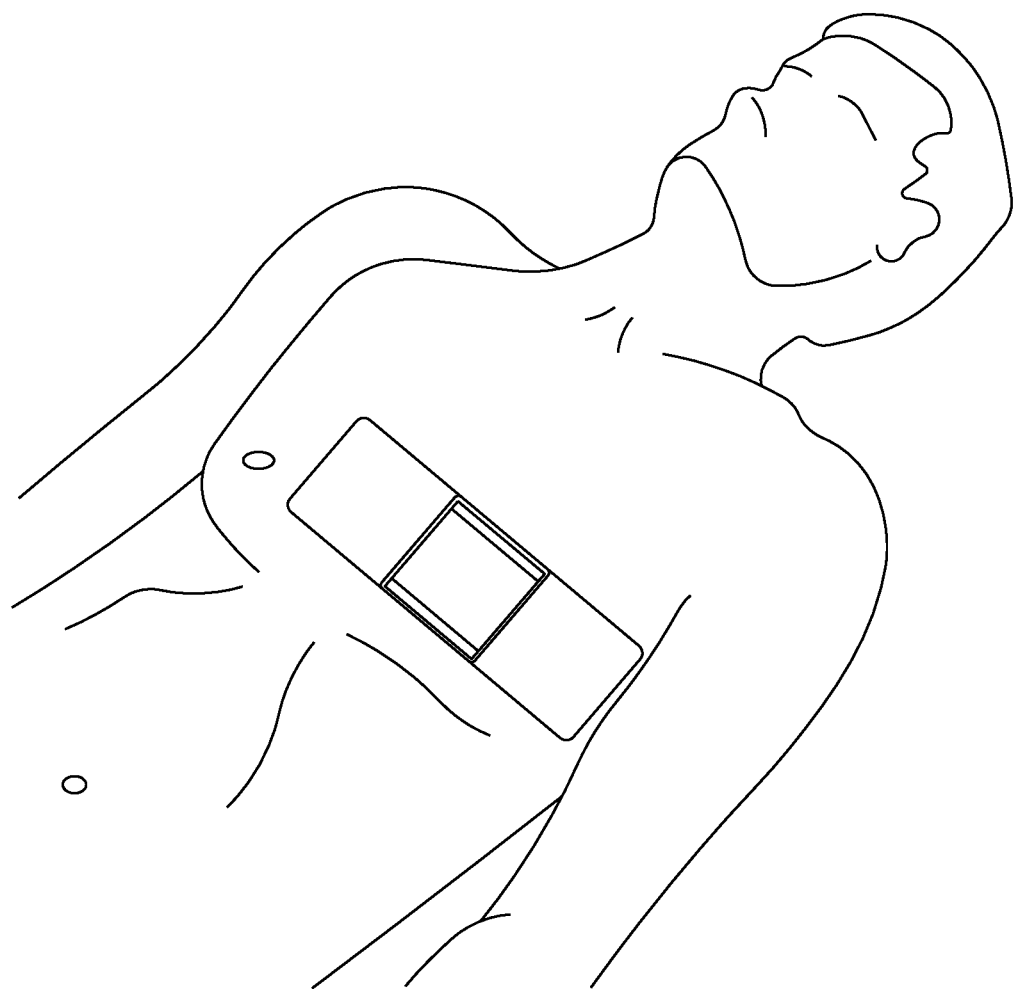
FIG. 3 is a pictorial of one concept of the SCA detection apparatus attached to the patient.
Figure 4:
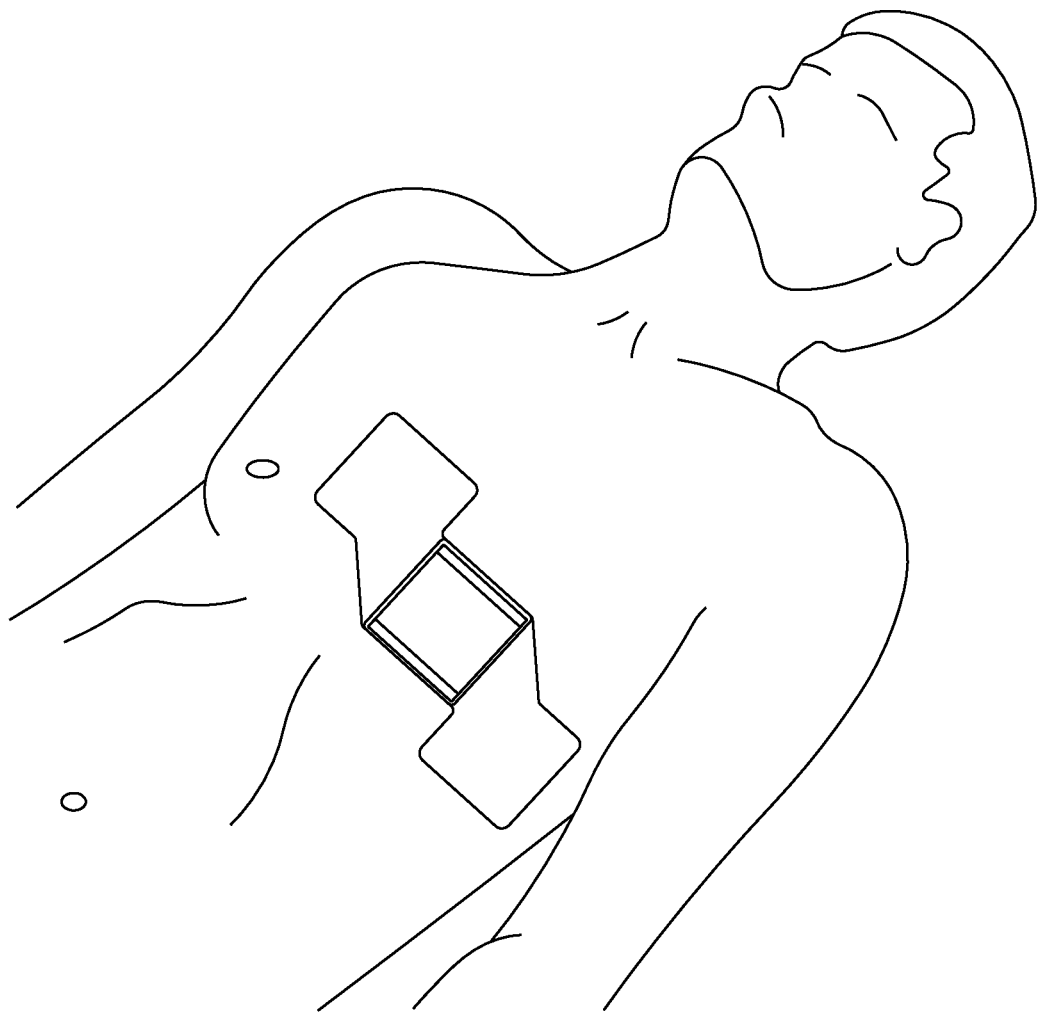
FIG. 4 is a pictorial of another concept of the SCA detection apparatus attached to the patient.
Figure 5:
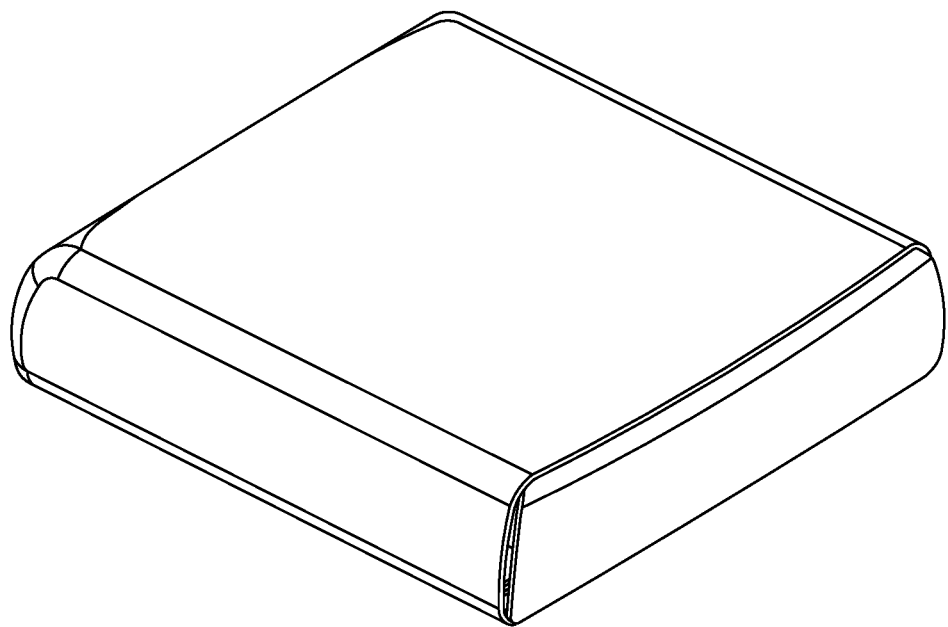
FIG. 5 is a pictorial of a concept of the SCA detection apparatus packaged and unopened.

FIGS. 3 and 4 show concepts of the SCA detection apparatus applied to the patient. The rescuer peels off a pad release liner (shown in FIG. 10) that exposes the electrodes. The rescuer then applies or "sticks" the device to the patient's exposed chest. Applying the device could be somewhat analogous to applying a large band-aid to the chest.

Figure 10:
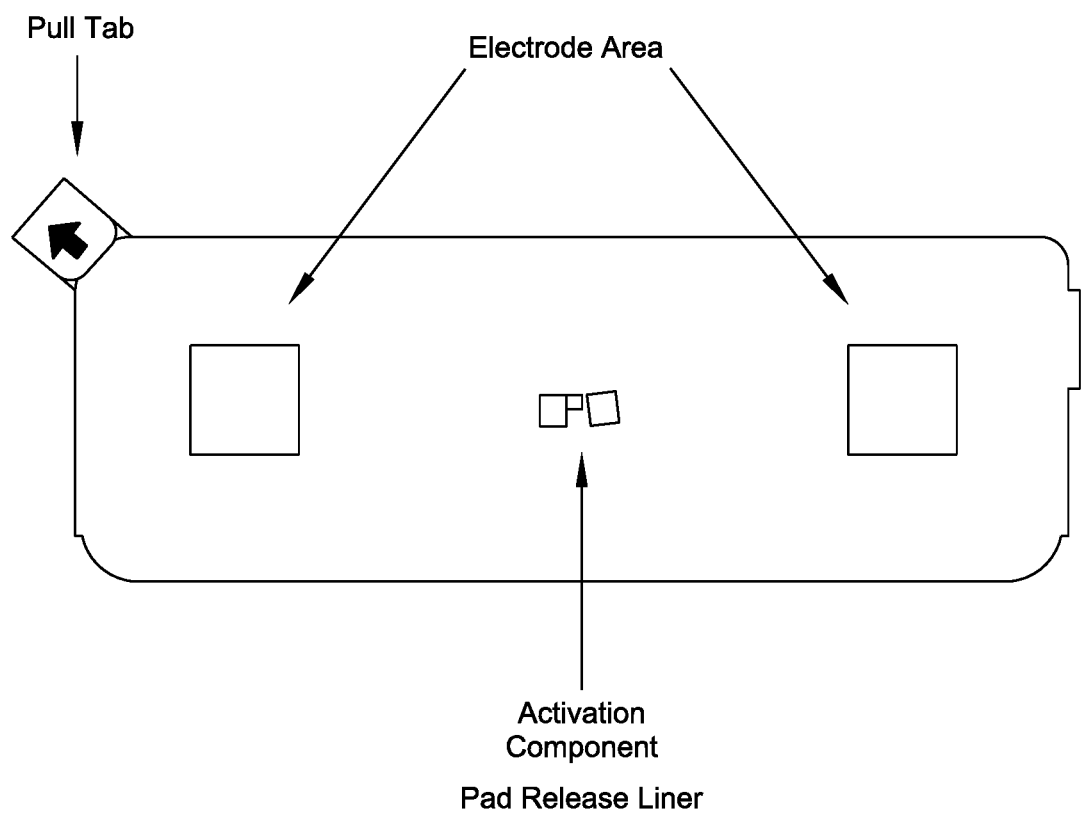
FIG. 10 is a pictorial of a concept the SCA detection apparatus with pad release liner detached.

The electrode area shown in FIG. 10 is square, but the area may be round or any other shape. The electrodes and surrounding pad may contain a hydrogel, electrically conductive adhesive or other compound which serves to connect the SCA detection apparatus to the patient and helps to hold or "stick" the device in place.

In accordance with another preferred form the present invention, the SCA detection apparatus release liner contains an "activation" component that causes the SCA detection apparatus to automatically power-on when the liner is removed. As those skilled in the art can appreciate, the component may be an active or inactive device. The activation component shown in FIG. 10 is a resistor.

In accordance with another preferred form the present invention, the SCA detection apparatus release liner may contain a different component, wire or resistor of a different value. This allows an identification of the type of SCA detection apparatus. In other words, there may be non-clinical versions that are used for training and allow a re-sealing, so that the training device can be used multiple times. The SCA detection apparatus communicates this information and allows the AED system to be put in "training mode" for specific configurations of the manufacturer's AED. Other versions of the pad release liner contain instructions and diagrams that show the rescuer where to place the SCA detection apparatus and how to remove the liner, etc.

Although these instructions are provided, removal of the pad release liner is easy and intuitive; the user simply peels the pull tab shown in FIG. 10 to remove the liner. In addition, the SCA detection apparatus need not be located exactly as shown in FIGS. 3 and 4, and will work in almost any position as long as it is located over the heart.

The SCA detection apparatus shown in FIG. 3 is in Lead-I configuration, but could also be adapted for Lead-II as shown in FIG. 4. As those skilled in the art can appreciate, the SCA detection device placement could be anterior-anterior, anterior-posterior or any other position placement as well. The SCA detection apparatus could be adapted 3-Lead, 5-Lead, 12-Lead or other configurations as well.

In accordance with one preferred form of the present invention, the SCA detection apparatus contains a wireless system and GPS that calls EMS, so that help is on the way. In other preferred forms of the present invention, the SCA detection apparatus may use Blue-tooth to "call" via a rescuer's cell phone. In yet another form of the present invention, the SCA detection apparatus instructs the rescuer to call 911 and has a label that instructs the rescuer where to find the nearest AED. The inventor notes that there may be many versions of the aforementioned apparatus to meet the economy of industry needs.

Figure 7:
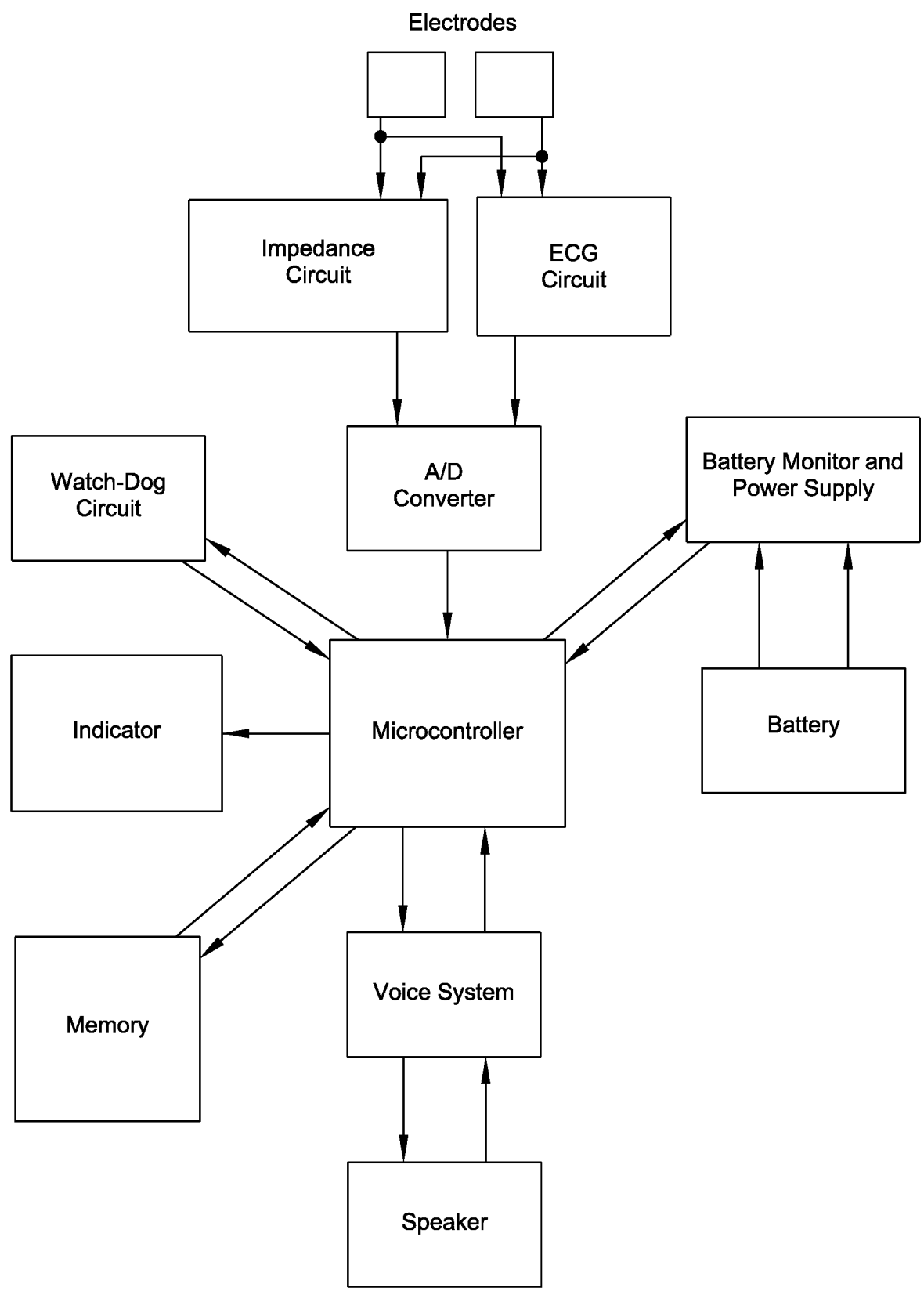
FIG. 7 is a block diagram of the SCA detection apparatus.

A block diagram of the SCA detection apparatus is shown in FIG. 7. The SCA detection apparatus controller circuit contains the necessary components and circuits to ensure the device works efficiently and reliably. Such examples of these are a watch-dog circuit which causes the status indication system to warn the rescuer of a malfunction of the controller or other circuits.

In accordance with the present invention, the watch-dog circuit and status indication system are configured so that if either fails, the status indication system indicates that the device is unusable, ensuring the entire system is failsafe. In accordance with one form of the present invention, the SCA detection apparatus runs a periodic self-test and uses the status indication system to notify the user of the results. The periodic self-test checks the SCA detection apparatus circuitry, controllers, batteries, etc.

In accordance with one preferred form of the present invention, the SCA Detection apparatus contains memory to store pertinent information. As those skilled in the can appreciate, the memory may be RAM, FLASH, EEPROM or any other type of volatile or non-volatile memory. The memory may also be internal and/or removable. Some examples of removable memory types are data cards, multimedia cards, synchronous digital, sticks or any other type known well by those skilled in the art.

In accordance with one preferred form of the present invention, the SCA Detection apparatus contains a battery and is self-powered. The battery contained within the apparatus may be removable, disposable, rechargeable, non-rechargeable, non-removable or any combination of the above well known by those skilled in the art. The apparatus also contains circuitry which allows measurement of the battery voltage and/or temperature. The apparatus is capable of storing this information in memory.

In accordance with one preferred form of the present invention, the SCA Detection apparatus contains an analog-to-digital converter (A/D) and other analog or digital circuitry.

In accordance with one preferred form of the present invention, the SCA Detection apparatus contains an ECG circuit capable of measuring the victim's electrical heart activity. The controller stores the victim's ECG in memory and runs an "advisory" algorithm using this information to detect or determine if the victim is in SCA. The data in memory may be removed later for post analysis of the event and to view details such as, but not limited to, the victim's heart rhythm (ECG), how long CPR was administered, self-test results, the time and location of the victim during the event, etc.

In accordance with one preferred form of the present invention, the SCA Detection apparatus can download the post analysis event data via wireless communications to another wireless system. The SCA detection apparatus only chooses to download the data from internal memory during non-clinical periods (when not applied to the patient) and/or after a clinical event has elapsed.

In accordance with one preferred form of the present invention, the SCA Detection apparatus contains an impedance analysis circuit to determine if the device is applied to the patient. The impedance analysis circuit may also measure the trans-thoracic impedance of the patient storing the measurement in memory.

The voice instruction system and status indication system contain visual and audible components to alert the user of a number of conditions. Examples of such conditions are alerting the rescuer that the patient requires therapy, alerting the user of low battery, other conditions within the device, etc.

The voice instruction system uses clear and easy-to-understand prompts for instructing the rescuer.

In accordance with another preferred form of the present invention, the SCA Detection apparatus contains a display for showing text, graphics, waveforms, video, etc.

In accordance with other preferred forms of the present invention, the SCA detection apparatus may contain other detection mechanisms, such as but not limited to: patient pulse and heart rate, patient temperature, patient blood pressure, patient blood oxygen level, etc. as is well understood by those skilled in the art or in the medical field. If SCA detection apparatus determines that CPR is necessary, the device instructs the rescuer to perform CPR and provides a pulsed tone and/or LED indicator for compressions. In accordance with one preferred form of the present invention, the SCA detection apparatus outer surface is contoured with a hand shape shown in FIG. 6 and is constructed to be pushed for chest compressions. The contoured hand shape on the top cover of the SCA detection apparatus allows the user to put one hand on the device and the other hand on top for performing CPR.

In accordance with one preferred form of the present invention, the SCA detection apparatus gives the rescuer feedback with regard to the CPR compressions they are performing.

In accordance with one preferred form of the present invention, the SCA detection apparatus contains the necessary components and circuitry for providing feedback to the user. There are many methods to provide feedback including the use of accelerometers, sensors, etc. well understood by those skilled in the art.

In accordance with one preferred form of the present invention, the SCA detection apparatus gives feedback to the rescuer during CPR. Some examples of feedback are, but not limited to, compression rate, compression depth, CPR duration, CPR respite, etc.

In accordance with one preferred form of the present invention, the SCA detection apparatus instructs the rescuer when to give mouth-to-mouth resuscitation breaths.

Figure 6:
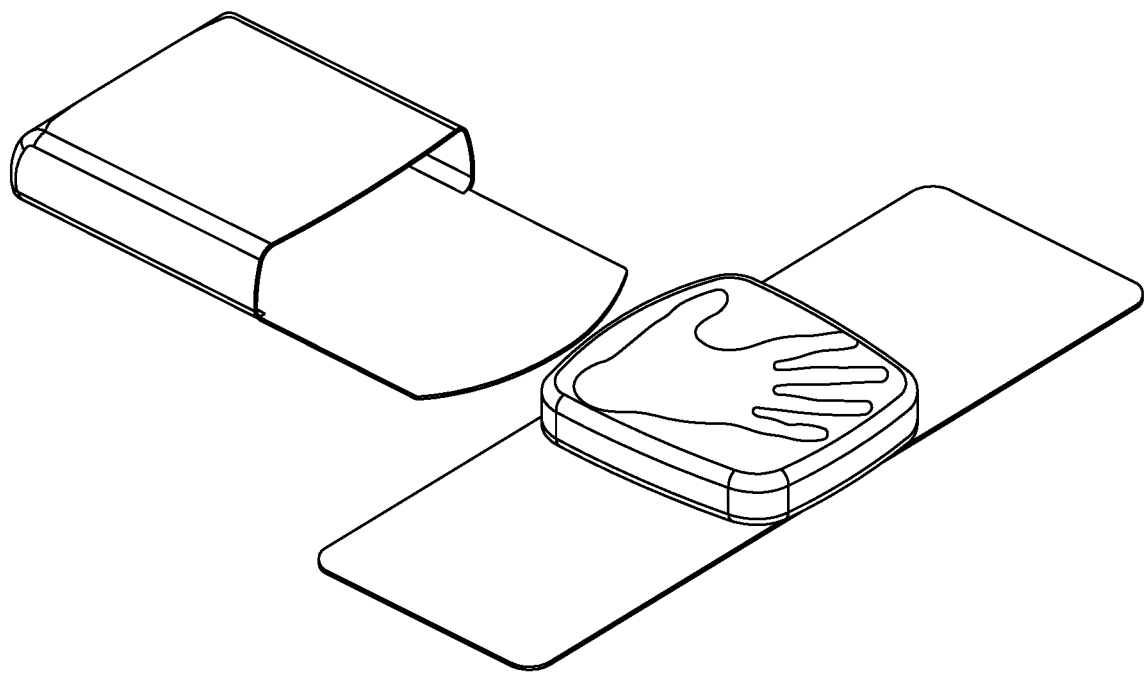
FIG. 6 is a pictorial of a concept of the SCA detection apparatus opened and ready to be applied to the victim.

The concepts shown in FIGS. 3 and 4 may contain some of the concept features shown in FIG. 6 or features that are completely different. Such examples of these features are handles, knobs, other manufacturer's CPR devices integrated into the apparatus, etc., or other devices that are used to perform CPR that are well known by those skilled in the art.

Once an AED has been located and brought to the victim, if SCA detection device instructs the rescuer to connect the AED, they simply open a small pouch on the device that contains an industry-standard length wire with a connector to allow connection to the AED. In accordance with one preferred form of the present invention, the SCA detection device already contains the defibrillation electrodes. The voice command system uses simple, clear instructions on how to connect the AED and to turn it on. The AED, which is not part of the SCA detection device, may be any manufacturer's AED, defibrillator, pacing device, etc. that is well understood by those skilled in the art or in the medical field. Most of the aforementioned devices contain an illuminated shock button that requires the user to press to deliver a defibrillation shock.

In accordance with one preferred form of the present invention, the SCA detection apparatus is compatible for use with the manufacturer's AED and electrode connection. In accordance with another preferred form of the present invention, the SCA detection apparatus contains an adaptor that allows connection to the manufacturer's AED.

In accordance with one preferred form of the present invention, the SCA detection apparatus AED connector is the industry standard connector per AHA/ERC guidelines, meaning that the AED and other manufacturers must comply with this connector by design or by the use of an adaptor.

In accordance with one preferred form of the present invention, the SCA detection apparatus senses that the AED is attached and enters "silent mode" so as not to confuse the rescuer with the prompts delivered by the AED.

In addition, as those skilled in the art can appreciate and in accordance with the present invention, the SCA detection apparatus affords the ability to first be used with one manufacturer's AED and then be used with a subsequent device by the use of an electrode connector adaptor or, in an ideal world, by using an industry standard connector. As those skilled in the art can appreciate, examples of such subsequent devices are, but not limited to, other manufacturer's AEDs, defibrillators, patient monitors, etc. This allows continuation of health care throughout the complete chain of rescue: from the initial rescue situation, to the transport of the patient to the hospital and transport within the hospital to the emergency care units.

In accordance with one preferred form of the present invention, the location apparatus contains all of the necessary blocks in the system blocks from FIG. 7. The location apparatus, however, does not connect to a patient, so certain blocks, such as ECG, Impedance and electrodes are not required.

Those skilled in the art can appreciate, the location apparatus otherwise may have mechanisms and functions that are quite similar to the SCA detection apparatus.

In accordance with one preferred form of the present invention, the location apparatus may be attached to the AED. In accordance with another preferred form of the present invention, the location apparatus may be integrated into the AED. In accordance with yet another preferred form of the present invention, the location apparatus may be attached to the AED, but may also be part of the enclosure system. In accordance with one preferred form of the present invention, the location apparatus is attached to the AED, but sits in a docking station or charging holder within the enclosure. This enables the apparatus to stay charged while sitting in standby mode. In accordance with one preferred form of the present invention, the location apparatus is connected to the enclosure's alarm system and triggers the alarm when "called" by the SCA detection apparatus. This alarm alerts an on-site rescuer that an event is occurring. It also helps rescuers locating the AED to find the device.

In accordance with another preferred form of the present invention, the location apparatus indication system contains the alarm system itself.

In accordance with one preferred form of the present invention, the location apparatus becomes detached from the docking station or charging holder when the AED is removed.

In accordance with one preferred form of the present invention, the location apparatus begins to instruct the rescuer of the location of the victim once the device is detached. As those skilled in the art can appreciate, the location apparatus gives verbal instructions similar to that of a personal GPS system, so the AED is quickly brought to the victim. If the rescuer is on-site, they can find the victim without having previous knowledge of the victim's location.

In accordance with one preferred form of the present invention, the location apparatus determines when it has reached the victim's location and enters a silent or muted mode.

In accordance with one preferred form of the present invention, the location apparatus, when "called" by the SCA detection apparatus, may indicate that the AED is out of service.

In accordance with one preferred form of the present invention, the location apparatus, when "called" by the SCA detection apparatus, may indicate that the AED is in use.

Figure 8:
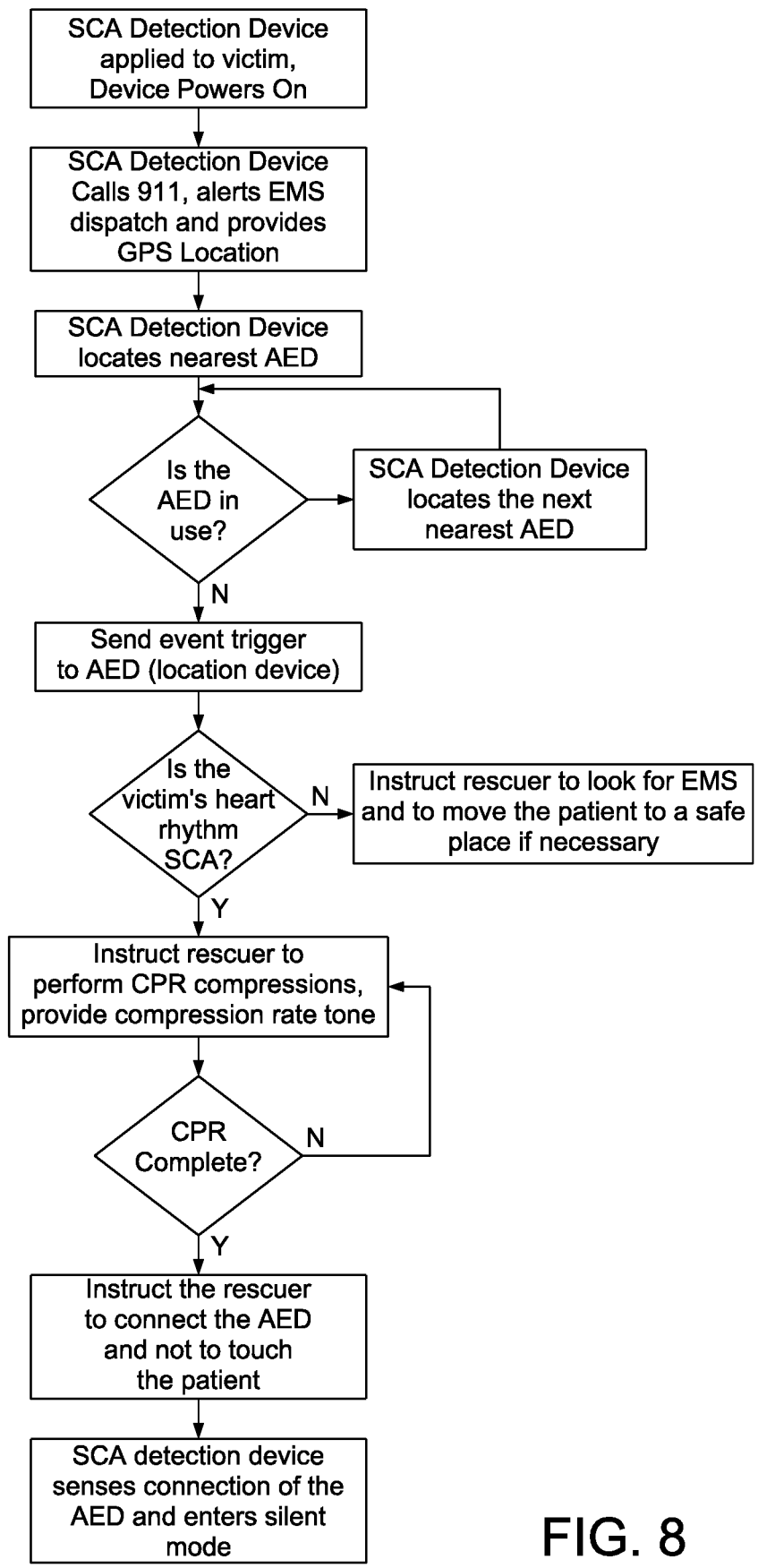
FIG. 8 is a flow diagram showing an example method used by the SCA detection device for expediting the rescue of victims experiencing SCA.

As shown in the example method in FIG. 8, if the SCA detection apparatus determines that the nearest AED is in use, it locates the next nearest AED. As those skilled in the art can appreciate, there may be many exceptions to this method in the event that the SCA detection apparatus determines that there may not be another AED located nearby and may use a pre-programmed parameter and/or an algorithm to decide if the AED is nearby.

In accordance with one preferred form of the present invention, the location apparatus when "called" by the SCA detection apparatus may indicate that the AED is needed in more than one location.

In U.S. patent application Ser. No. 11/978,261, filed Oct. 29, 2007 by Kyle R. Bowers for AUTOMATED EXTERNAL DEFIBRILLATOR (AED) SYSTEM WITH MULTIPLE PATIENT WIRELESS MONITORING CAPABILITY FOR USE IN MASS CASUALTY INCIDENTS, and in U.S. patent application Ser. No. 12/772,216, filed Mar. 11, 2010 by Kyle R. Bowers for WIRELESS MONITORING APPARATUS USED IN CONJUNCTION WITH AN AUTOMATED EXTERNAL DEFIBRILLATOR (RED) SYSTEM FOR MULTIPLE PATIENT RESCUE DURING MASS CASUALTY INCIDENTS, which patent applications are hereby incorporated herein by reference, the inventor teaches that a single AED can be used to treat several patient in a multiple or mass casualty incident. The same teachings can be applied to preferred forms of the present invention. As discussed earlier and looking at FIG. 1, there is no limitation to the number of branches in the system network. In fact, the network can be seen as a web or even a grid connecting several networks. As those skilled in the art can appreciate, with current wireless and GPS technologies, several known methods can be applied to connect one or more or all of the apparatuses, which includes AEDs or any other compatible device that has or contains a location apparatus. In accordance with one preferred form of the present invention, the method used by the disclosed apparatuses decides which devices they will communicate with in pairs before an event occurs. In other words, looking back in FIG. 8, this example method could be modified to have already decided which AED(s) are nearby.

In accordance with yet another preferred form of the present invention, the method used by the disclosed apparatuses decides which devices they will communicate with in pairs during an event. In other words, the method can decide either before an event (i.e., both devices currently not in use and logistically close) and/or decide during an event (i.e., one device currently in use).

In accordance with one another preferred form of the present invention, the method used by the one or more of the disclosed apparatuses decides which devices they will communicate with in multiples before and/or during an event. In other words, one or more devices on the network decide logistically, in a prioritized scheme, which other devices they will communicate with regardless if one or more devices are in use. In the event of more than one casualty, the apparatuses can find one or more AEDs in nearby locations, so that one or more victims can be treated simultaneously.

In accordance with yet another preferred form of the present invention, the method used by the one or more of the disclosed apparatuses decides that even though the AED is currently in use in one location, it will be needed thereafter for a subsequent event. In other words, in a mass casualty event, one or more SCA detection apparatus(es) decide that even though there are multiple events occurring simultaneously, that a single AED should be used in a prioritized sequence, i.e., triage situation. This information would be communicated in concert with the locating apparatus. Looking back at FIG. 8, the example method would be appropriately modified for a second event. As those skilled in the art can appreciate, the second device may decide to skip some blocks shown in FIG. 8 based on information at the time of the event or in the timing of a combination of events.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

The invention claimed is:

1. A method for expediting the rescue of a victim experiencing sudden cardiac arrest (SCA), wherein the method wirelessly connects a sudden cardiac arrest (SCA) detection apparatus located with the victim to a location apparatus located with an automatic external defibrillator (AED), wherein the SCA detection apparatus comprises one or more electrodes for attachment to the victim, the method comprising:
   (1) analyzing the victim to detect whether the victim is in SCA;
   (2) calling for help, wherein the call for help is performed in accordance with a list of prioritized numbers, with the SCA detection apparatus calling a secondary number if there is no answer at a primary number, and further wherein the call for help is performed as a background task so as not to affect further operation of the SCA detection apparatus;
   (3) if SCA is detected, guiding a rescuer through performing cardiopulmonary resuscitation (CPR);
   (4) locating a nearby AED by communicating with the location apparatus located with the nearby AED;
   (5) indicating the location of the victim to the nearby AED;
   (6) guiding at least one of the rescuer and a second rescuer to the location of the nearby AED; and
   (7) guiding at least one of the rescuer and the second rescuer on how to connect the nearby AED to the SCA detection apparatus;
   wherein steps (1)-(3) and (7) are performed by the SCA detection apparatus, wherein step (4) is performed by the SCA detection apparatus and the location apparatus, and further wherein steps (5) and (6) are performed by at least one of the SCA detection apparatus and the location apparatus.

2. The method according to claim 1 wherein the SCA detection apparatus further comprises:
   at least one battery;
   a wire and connector for connection to an AED;
   a status indication system;
   a voice messaging system;
   at least one controller;
   controls, components and circuitry to allow wireless communications; and
   controls, components and circuitry to allow Global Positioning System (GPS).

3. The method according to claim 2 wherein the SCA detection apparatus uses the voice messaging system to report the location of the nearby AED.

4. The method according to claim 3 wherein the SCA detection apparatus uses the voice messaging system and indicators to instruct the rescuer on performing CPR.

5. The method according to claim 4 wherein the SCA detection apparatus uses the voice messaging system and indicators to give the rescuer feedback on the CPR they are performing.

6. The method according to claim 4 wherein the SCA detection apparatus uses the voice messaging system and indicators to give the rescuer feedback on CPR compression rate and depth.

7. The method according to claim 2 wherein the SCA detection apparatus uses the voice messaging system to instruct at least one of the rescuer and the second rescuer on how to connect an AED.

8. The method according to claim 1 wherein the SCA detection apparatus further comprises controls and circuitry to measure and analyze an electrocardiogram (ECG) signal of the victim.

9. The method according to claim 1 wherein the SCA detection apparatus further comprises controls and circuitry to measure and analyze a transthoracic impedance signal of the victim.

10. The method according to claim 1 wherein the SCA detection apparatus further comprises controls and circuitry to measure and analyze one or more of the victim's:
   temperature;
   blood oxygen level;
   blood pressure;
   pulse; and
   heart rate.

11. The method according to claim 1 wherein step (1) comprises analyzing an ECG signal of the victim to determine if a heart rhythm of the victim is shockable.

12. The method according to claim 11 wherein the SCA detection apparatus determines if the heart rhythm of the victim is shockable and uses a voice messaging system to report the results.

13. The method according to claim 1 wherein the SCA detection apparatus measures and stores victim data in internal memory.

14. The method according to claim 13 wherein the SCA detection apparatus upon request transmits victim data stored in internal memory to another wireless device during non-clinical periods.

15. The method according to claim 1 wherein the SCA detection apparatus enters a silenced mode when the AED is connected.

16. The method according to claim 1 wherein the SCA detection apparatus further comprises a removable release liner having an activation component which causes the apparatus to automatically power-on when the release liner is removed from the apparatus.

17. The method according to claim 1 wherein the SCA detection apparatus is configured to run an algorithm to detect whether the victim is in SCA.

18. The method according to claim 1 wherein the location apparatus contains visual and audible components to alert the rescuer or the second rescuer of one or more conditions when triggered, wherein the one or more conditions comprises at least one of the location of the victim and the status of the nearby AED.

19. The method according to claim 1 wherein the location apparatus is configured to enter a silent mode when it reaches the victim's location.

20. The method according to claim 1 wherein the location apparatus is configured to indicate whether the AED is out of service or in use when contacted by the SCA detection apparatus.

* * * * *